(12) United States Patent
Glucksman et al.

(10) Patent No.: US 7,270,641 B2
(45) Date of Patent: Sep. 18, 2007

(54) APPARATUS FOR ABRADING HAIR AND EXFOLIATING SKIN

(75) Inventors: Dov Z. Glucksman, Danvers, MA (US); Gary P. McGonagle, Lynn, MA (US); Laura J. Nickerson, Fitchburg, MA (US)

(73) Assignee: Appliance Development Corporation, Danvers, MA (US)

( * ) Notice: Subject to any disclaimer, the term of this patent is extended or adjusted under 35 U.S.C. 154(b) by 326 days.

(21) Appl. No.: 10/932,185

(22) Filed: Sep. 1, 2004

(65) Prior Publication Data

US 2006/0047234 A1 Mar. 2, 2006

(51) Int. Cl.
*A61H 7/00* (2006.01)

(52) U.S. Cl. .................... 601/112; 601/84; 601/87; 606/133

(58) Field of Classification Search .......... 601/72, 601/80, 84, 87, 89, 93–95, 112–114, 136, 601/138, 139–142; 606/131, 133; 604/289, 604/291; 15/23, 24, 28, 29, 34, 97.1
See application file for complete search history.

(56) References Cited

U.S. PATENT DOCUMENTS

| | | | |
|---|---|---|---|
| 1,577,751 A * | 3/1926 | Paschall | 601/112 |
| 2,950,683 A | 8/1960 | Nilsson | |
| 2,993,311 A | 7/1961 | West | |
| 3,581,392 A | 6/1971 | Hubner | |
| 5,377,699 A | 1/1995 | Varnum | |
| 5,950,268 A * | 9/1999 | Murphy et al. | 15/28 |
| 5,983,501 A | 11/1999 | Isumi | |
| 6,244,943 B1 | 6/2001 | Bohler et al. | |
| 6,277,128 B1 | 8/2001 | Muldner | |
| 6,471,712 B2 | 10/2002 | Burres | |
| 6,575,924 B2 * | 6/2003 | Wevers et al. | 601/112 |
| 2003/0125754 A1 | 7/2003 | Davis et al. | |

\* cited by examiner

*Primary Examiner*—Quang D. Thanh
(74) *Attorney, Agent, or Firm*—George A. Herbster (57) ABSTRACT

Apparatus for abrading hair and exfoliating skin. An electric motor drive produces rotation at three transmission outputs. A universal joint connects each motion transmission output to a disk for supporting annular abrasive pads. The abrasive disks and pads are free to swivel to maximize surface contact between the abrasive pad and skin during use.

9 Claims, 8 Drawing Sheets

APPARATUS FOR ABRADING HAIR AND EXFOLIATING SKIN

BACKGROUND OF THE INVENTION

1. Field of the Invention

This invention generally relates to personal skin care apparatus and more particularly to apparatus for removing hair and exfoliating skin by abrasion.

2. Description of Related Art

There are diverse categories of personal skin care devices for removing hair and exfoliating skin. Some hair removal, or depilation, apparatus plucks the hair from the body often in conjunction with electrolysis, waxing or other chemical treatment. Bleaching and shaving represent other approaches to depilation. Exfoliation apparatus is in another category and has included scrubbing devices, the use of chemical agents and cutting apparatus.

This invention is particularly directed to depilation and skin exfoliation achieved by abrasion techniques. For example, U.S. Pat. No. 5,377,699 to Varnum discloses hair abrading apparatus with a drum having an abrasive surface. A protective screen or cap positions hair for contact with the abrasive surface to protect the skin. This apparatus abrades hair, but does not exfoliate the skin.

U.S. Pat. No. 6,277,128 to Muldner discloses skin abrasion treatment apparatus in which a nozzle directs abrasive material across a slot formed in an abrasion chamber along a generally helical path. The paths are either vertically or horizontally oriented with respect to an abrasion nozzle. As the abrasion material passes through the slot, it abrades hair and exfoliates the skin.

U.S. Pat. No. 6,471,712 to Burres discloses a dermabrasion and skin care apparatus for abrading, cleaning, massaging, buffing or otherwise treating the skin, fingernails, toenails or other body surfaces. The device includes a drum driven by an electric motor. The drum contacts the skin surface.

U.S. Patent Application Publication No. U.S. 2003/1025754 to Davis et al. discloses an electrical hair buffing apparatus that provides both depilation and exfoliation. This device includes a pair of closely adjacent counter-rotating abrasive surfaces that press against the skin to abrade the hair and exfoliate the skin. The surfaces are adapted for continual, alternating movement in counter-rotating directions at the surface of the skin. In one specific embodiment two concentric counter-rotating abrasive surfaces are used.

These and other prior art devices require care during use because they place abrasive surfaces into contact with the skin. Drums present a relatively narrow straight-line contact against uneven skin surfaces. Allowing such a unit to dwell while rotating or applying too much pressure onto the skin can result in skin damage to portions of the skin. Flat disks, while potentially providing somewhat broader area of contact, can still remove excessive skin if they are allowed to dwell at a particular position particularly in the area near the center of the disk. If a disk is not completely flat against the skin, but tilts, more pressure is applied against the edges. The disk can then cause edge burn. With counter-rotating disks it is possible for the disks grab the skin and apply forces in opposite directions at adjacent tangents. This can stress the outer skin surface and cause skin damage where the disks are proximate each other. If handled by professionals who are trained and experienced, these problems can be minimized. However, the occasional user, as for example an individual using these devices on their own body, can suffer abrasions or uneven treatment of the skin due to the characteristics of the abrading device and the uneven surface of the skin.

SUMMARY

Therefore it is an object of this invention to provide skin care apparatus for hair removal and skin exfoliation as a personal care device.

Another object of this invention is to provide skin care apparatus for abrading hair and exfoliating skin that minimizes the potential for skin damage.

Still another object of this invention is to provide skin care apparatus for abrading hair and exfoliating skin that minimizes skin damage caused when the apparatus dwells at a particular location on the skin.

Yet another object of this invention is to provide skin care apparatus for abrading hair and exfoliating skin that minimizes skin damage caused by edges of a disk.

Still yet another object of this invention is to provide skin care apparatus for abrading hair and exfoliating skin that minimizes skin damage due to any overstressing of portions of the skin.

Yet still another object of this invention is to provide skin care apparatus for abrading hair and exfoliating skin adapted for low-cost manufacture.

In accordance with one aspect of this invention, apparatus for abrading hair and exfoliating skin includes a housing for defining the form of the apparatus and a drive in the housing for producing rotary motion of an output shaft about a drive axis. A switch on the housing enables an operator to control the drive. A motion transfer mechanism converts the drive output shaft rotation into rotation of each of a plurality of spaced, parallel transfer outputs about output axes. A disk with a shaft that terminates in a spherical head connects to each spaced, parallel transfer output and is adapted for carrying a pad with an abrasive surface. A disk with a shaft that terminates in a spherical head connects to each spaced, parallel transfer output and is adapted for carrying a pad with an abrasive surface. A universal joint couples the rotary motion of each transfer output to a corresponding disk. Each spherical head includes a slot therethrough and each universal joint includes a pin affixed to the transfer means that passes through the slot.

In accordance with another aspect of this invention, apparatus for abrading hair and exfoliating skin includes a housing that defines the form of the apparatus. An electric motor in the housing rotates an electric motor output shaft. A switch on the housing enables an operator to energize the electric motor and operate the apparatus. The apparatus also includes three abrasive pad support disks. Each disk has a rounded annular section for supporting an annular abrasive pad whereby the abrasive pad presents a curved annular abrasive surface to the skin. A shaft extends from the abrasive pad support to a slotted spherical head. A motion transfer gear train interconnects the electric motor output shaft to the three abrasive pad support disks. The gear train includes an input shaft connected to the electric motor output shaft and three spaced driving gears thereon that act as transfer outputs and that rotate about three parallel motion transfer gear train output axes. An idler gear rotates about an idler gear axis with a first gear connection to the input shaft and a second gear connection to each of the outputs. Energization of the electric motor causes the outputs to rotate in the same direction with an angular velocity that is less than the angular velocity of the electric motor output shaft. A bearing block on each driving gear captures a spherical head thereby to retain a disk on the output shaft with the freedom to rotate in the block. A pin attaches to each driving gear and extends through the bearing block and spherical head to translate rotational motion of the driving gear into rotational motion of the disk while allowing the disk to swivel in the block.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
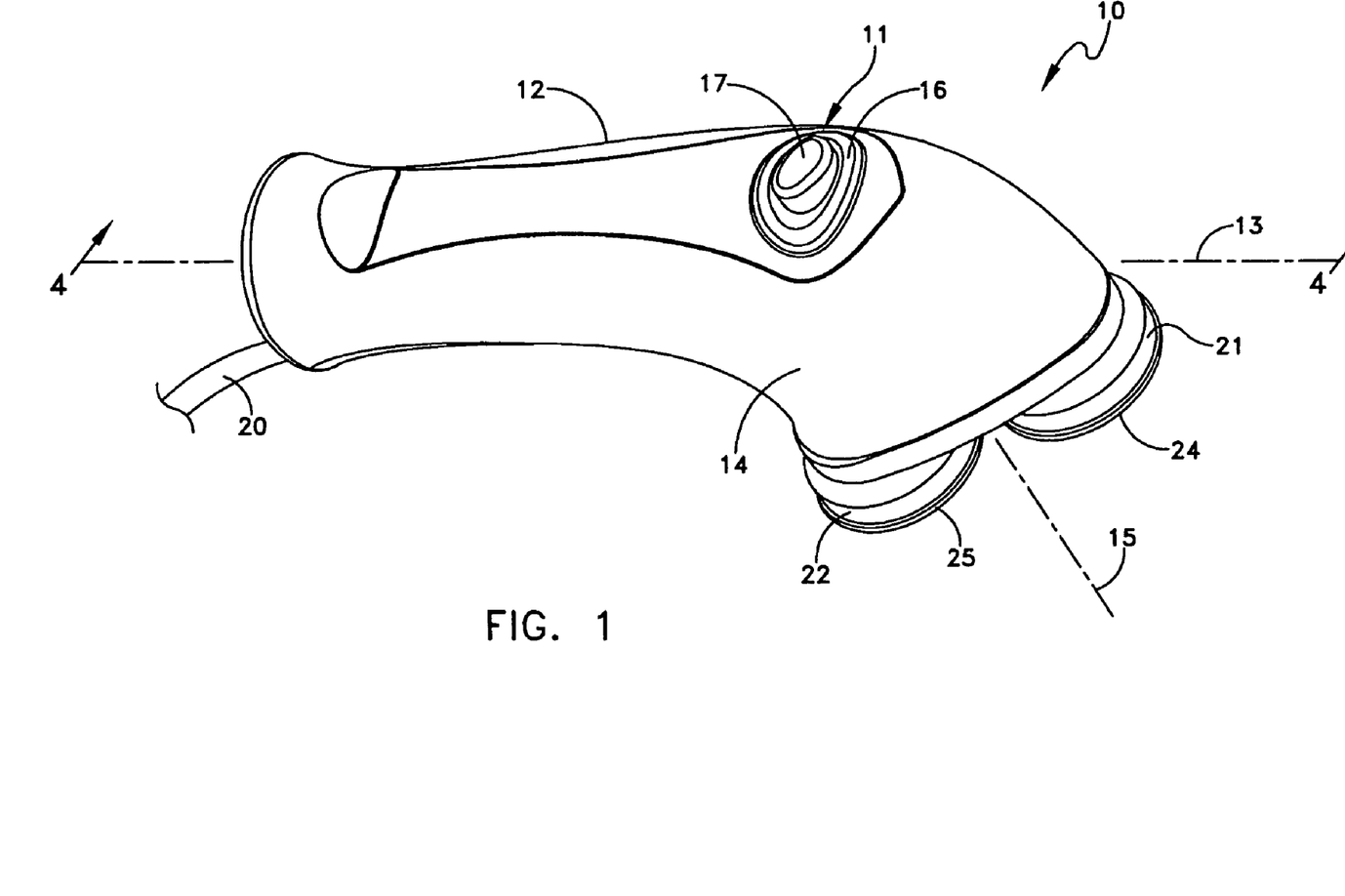
FIG. 1 is a perspective view of a hair abrading and skin exfoliating apparatus embodying this invention.
Figure 2:
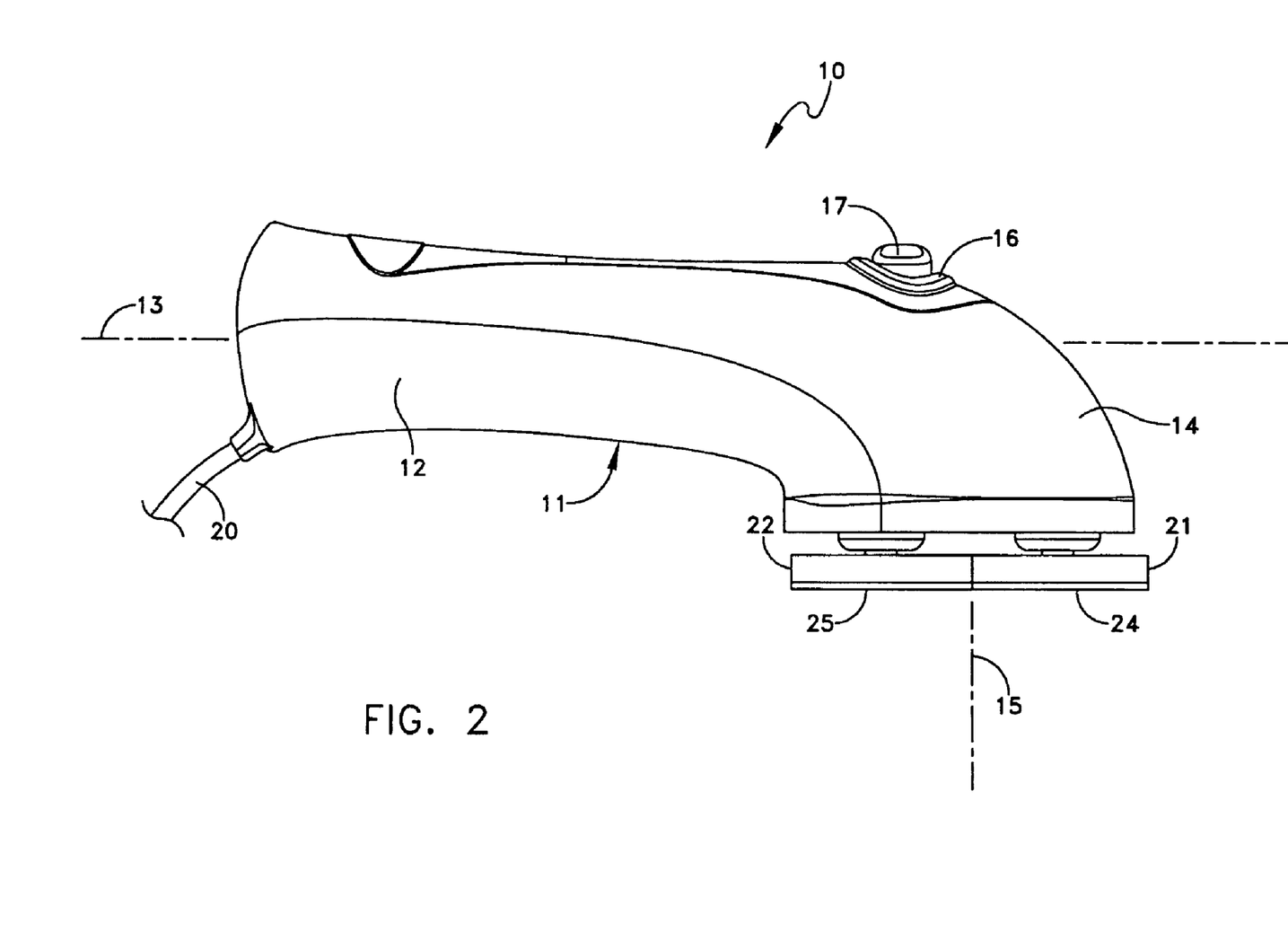
FIG. 2 is a side view of the apparatus shown in FIG. 1.
Figure 3:
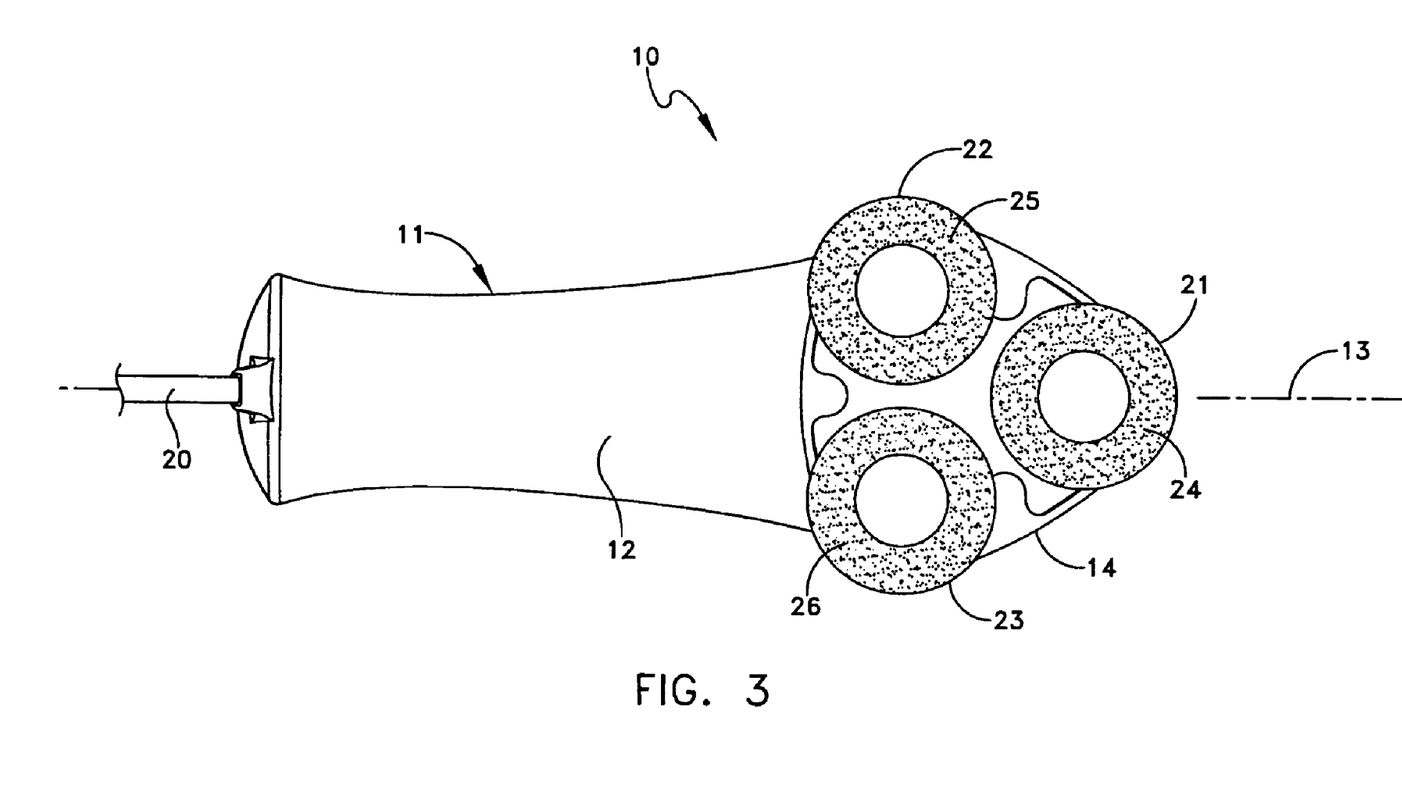
FIG. 3 is a bottom view of the apparatus shown in FIG. 1.

A specific embodiment of this invention is depicted in FIGS. 1 through 3 as skin care apparatus 10 in the form of a device that can abrade hair and exfoliate skin. It includes a housing 11 that defines the overall shape and configuration of the skin care apparatus. In this particular embodiment the housing 11 defines a handle 12 that extends along a handle axis 13 and a head 14 that extends along a head axis 15. In this specific embodiment the handle axis 13 and the head axis 15 intersect.

The handle shape is adapted to enable an individual to clasp the apparatus 10 comfortably and activate a switch assembly 16 particularly by moving a switch slider 17 transversely to the axis between on and off positions. The switch slider 17 controls an electric drive, as shown in more detail later, powered from an electrical source represented as a power cord 20.

When the electric drive is energized, a motion transfer gear train, also within the housing 11, rotates disks 21, 22 and 23. Each disk carries an abrasive pad. In a preferred embodiment and for reasons described later, the pad is annular. Annular pads 24, 25 and 26 are shown being carried by disks 21, 22 and 23, respectively. The motion transfer gear train within the housing 11 thus converts rotating motion of the drive into rotating motion of the disks 21, 22 and 23 with their respective pads 24, 25 and 26 about transfer output axes parallel to the head axis 15.

As will also become more apparent, each disk and pad, such as the disk 21 and abrasive pad 24, is free to swivel about a corresponding transfer output axis independently of the other disks. That angle is selected so that the face of any disk with its abrasive pad can swivel to better conform to adjacent portions of the skin. As also particularly evident from FIG. 3, the annular abrasive disks 24, 25 and 26 are spaced from each other thereby minimizing any tension placed upon the skin by counter-rotating portions of adjacent disks.

In use an individual grasps the apparatus by the handle 12, positions the thumb at the switch slider 17 and places the pads on an area to be treated. Then the person moves the switch slider 17 to activate the apparatus so the abrasive pads 24, 25 and 26 rotate. As the unit is moved over the skin, the pads adapt to changes in the skin profile as they each abrade hair and exfoliate the skin.

The pads have an annular shape, so there is less tendency of an adverse reaction of a solid disk pad by central drilling. The individual merely needs to move the device back and forth across the skin in order to complete the treatment, but the precision of this motion required by prior art devices is relaxed because the apparatus 10 is more tolerant of overly long dwell times or tilting that might cause a disk edge to cut into the skin.

Figure 4:
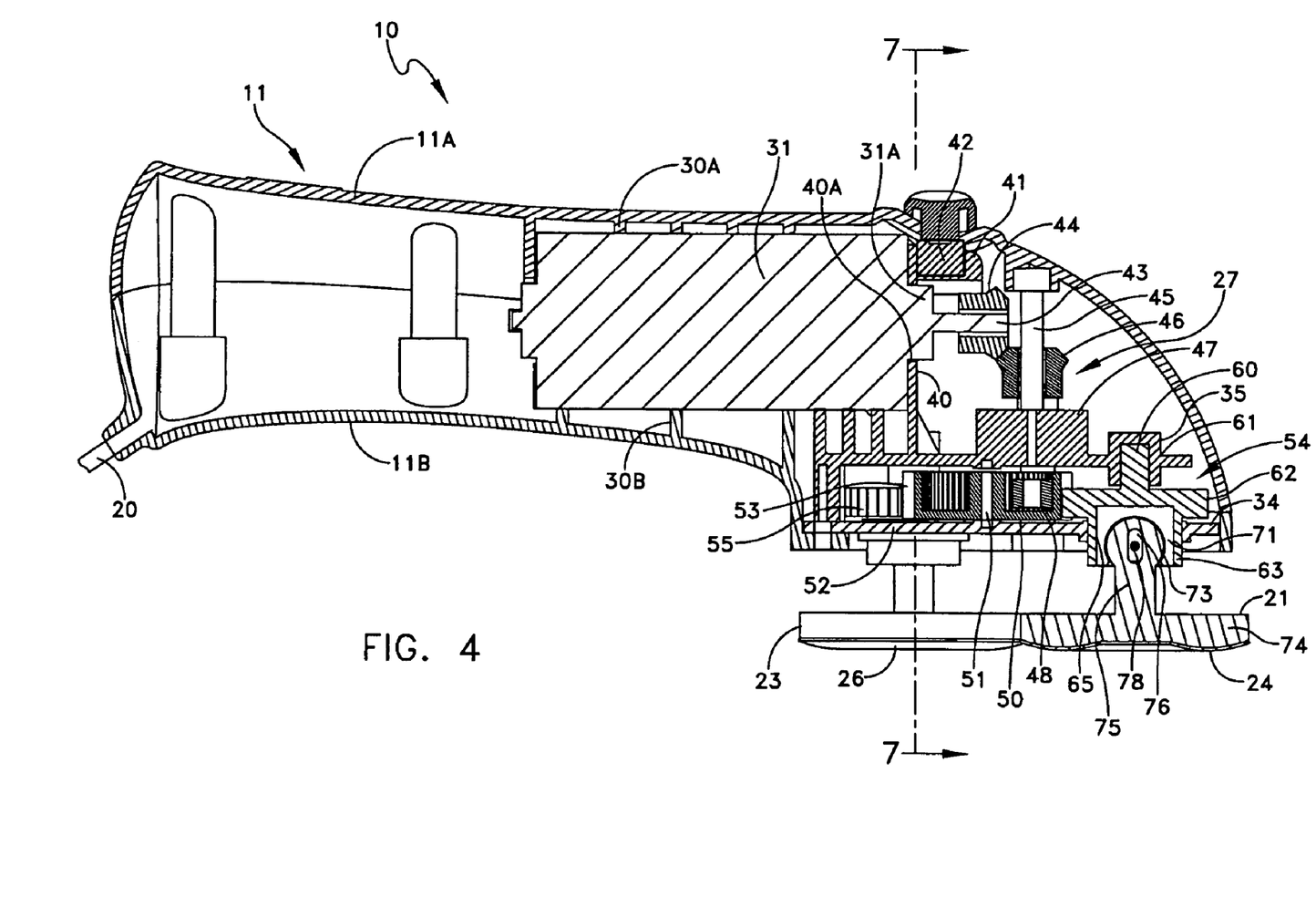
FIG. 4 is a cross-sectional view taken along lines 4-4 in FIG. 1.
Figure 5:
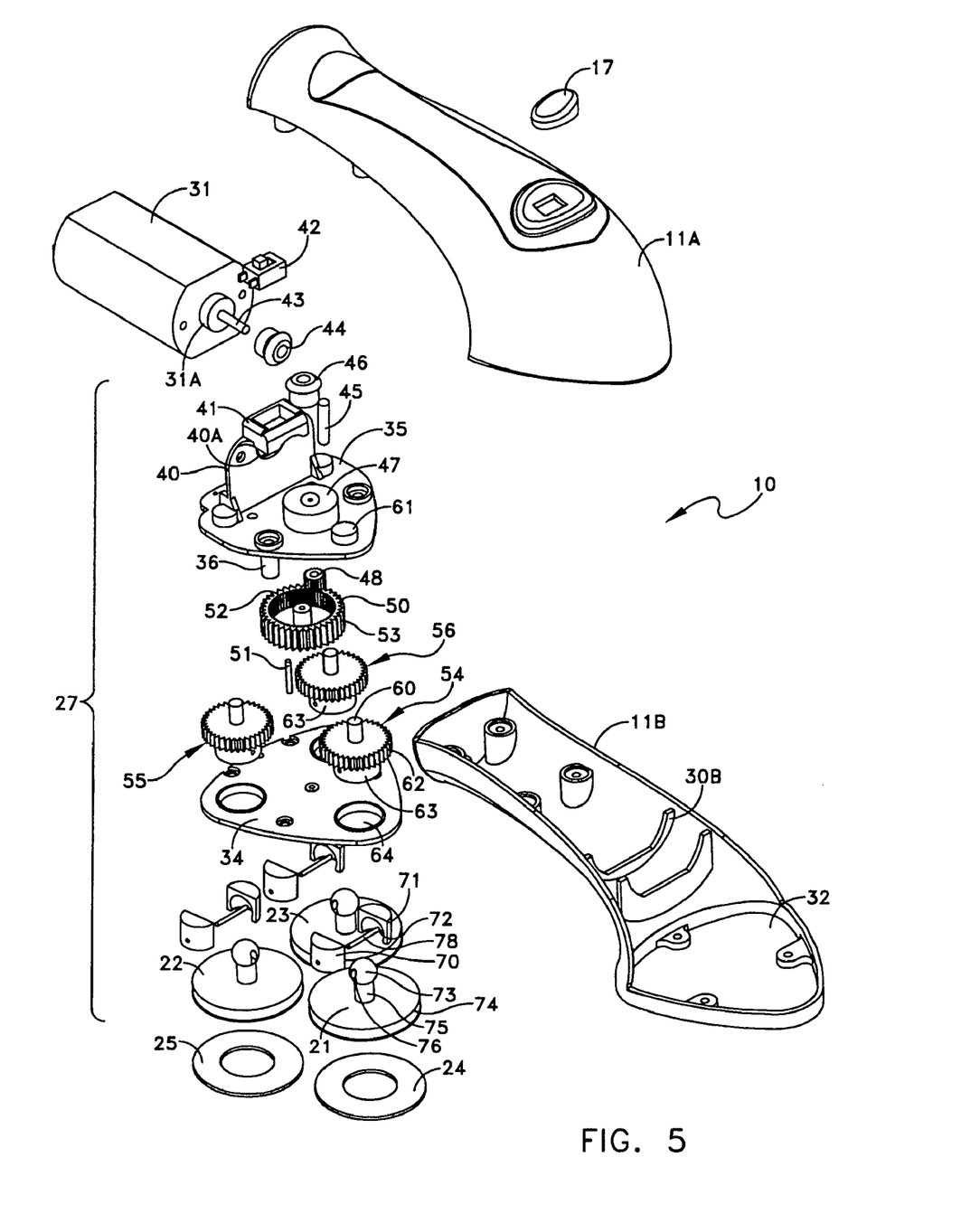
FIG. 5 is an exploded view of the apparatus of FIG. 1.

Now referring to FIGS. 4 through 7, particularly FIG. 5, the apparatus 10 includes a motion transfer gear train 27. In this particular embodiment the housing 11 includes an upper unit 11A and a bottom unit 11B for supporting the motion transfer gear train 27. The upper housing unit 11A and bottom unit 11B include cradle assemblies 30A*a* and 30B that capture a small, compact motor 31. In one particular embodiment the motor 31 is a 120 volt, 8,000 rpm, permanent magnet motor.

As shown most clearly in FIG. 5, the bottom housing unit 11B includes an opening 32. In this particular embodiment the opening 32 has a triangular shape. Inwardly projecting tabs 33 receive and support a bottom bearing plate 34. The bottom bearing plate 34 supports a top bearing plate 35 in a spaced parallel relationship by means of posts 36 (only one is shown in FIG. 5). The bearing plates 34 and 35 carry the various gears and shafts that constitute the motion transfer gear train 27.

More specifically, the upper bearing plate 35 includes an upstanding plate 40 that is perpendicular to the plane of the upper bearing plate 35. This structure positions the motor 31 by means of a shoulder 31A that is received in an opening 40A in the plate 40 as most clearly shown in FIGS. 4 and 7. Other fasteners attach an end plate of the motor 31 to the plate 40 in a manner well known in the art.

As shown in FIGS. 4 and 5, the vertical plate 40 also supports a switch housing 41 that carries an electrical slider switch 42 that interacts with the switch slider 17 on the upper handle housing 11A thereby to provide an operator-controlled switch for energizing the motor 31. The interconnections among the power cord 20 in FIGS. 1 through 4 and the electric motor 31 and slider switch 42 are not shown, but are well known in the art.

Figure 6:
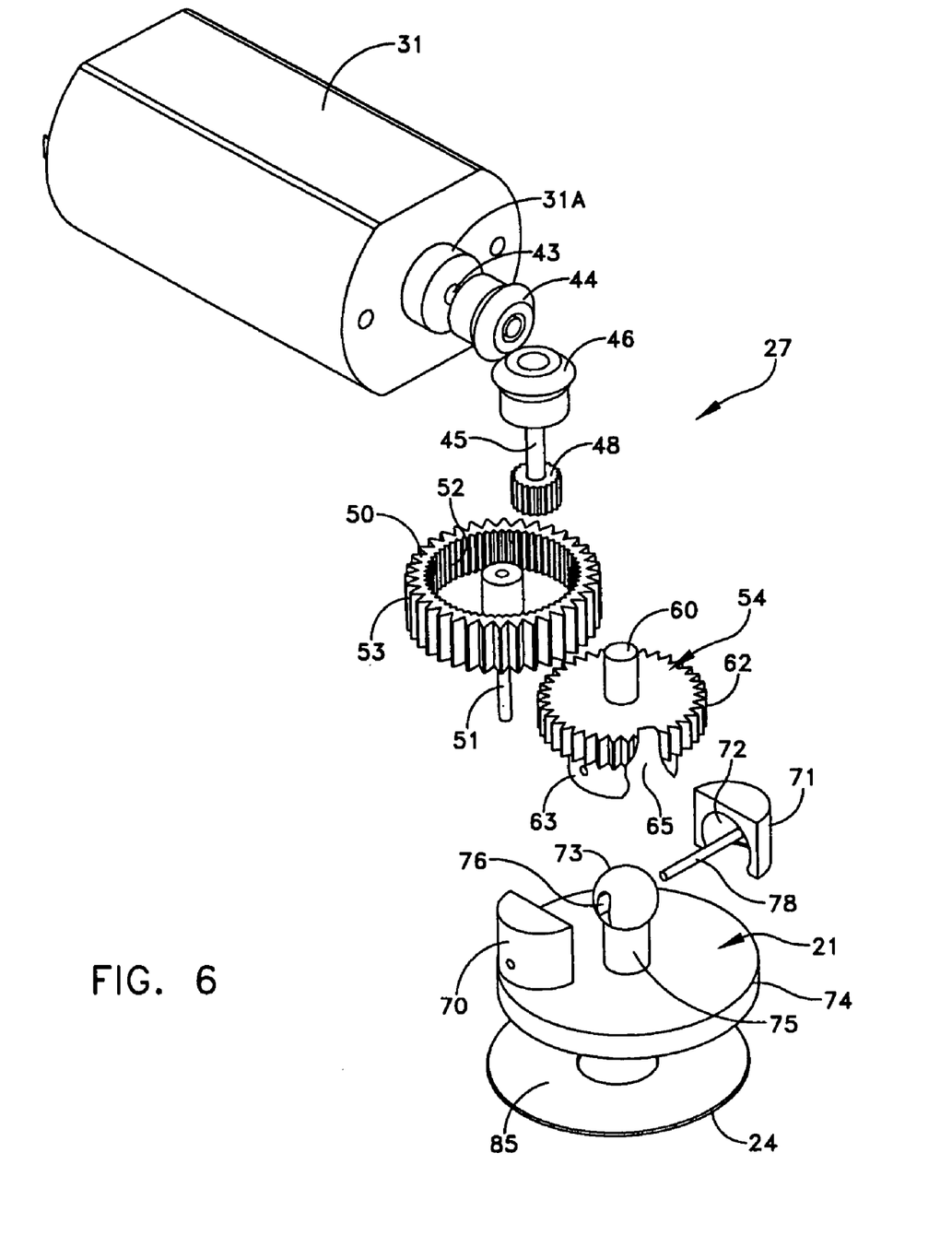
FIG. 6 is an exploded view showing the main components of a motion transfer mechanism for one disk incorporated in the apparatus of FIG. 1.

In whatever form an output shaft 43 from the motor 31 constitutes a drive output shaft. In the embodiment of FIGS. 4 through 6, a motor pinion 44 on the motor shaft 43 drives an input shaft 45 to the motion transfer gear train 27 through an input gear 46. The input shaft 45 extends through a bearing block 47 formed on the bearing plate 35 and rotates a drive pinion 48. In this specific embodiment, axes for the motion output shaft 43 and input shaft 45 intersect essentially at a right angle. Various methods are well known to those skilled in the art for accommodating different angular relationships between the motor shaft 43 and the input shaft 45.

The bearing plates 34 and 35 also support an idler gear 50 for rotation about an idler gear shaft 51. The idler gear 50 includes internal teeth 52 that engage the driving pinion 48.

In this particular embodiment the axes of the shafts 45 and 51 are offset and the relative dimensions for the outside diameter of the driving pinion 48 and the internal dimension of the internal teeth 52 provide speed reduction.

As the idler gear 50 rotates, its external teeth 53 drive gear assemblies 54, 55 and 56. As each of these structures is identical, reference is particularly made to FIGS. 5 and 6 which depict the gear assembly 54 in greater detail. In the gear assembly 54, a shaft 60 rotates in a bearing block 61 in the upper bearing plate 35. The shaft 60 carries an externally toothed gear 62 and a cylindrical body portion 63. The body portion 63 is at least partially coextensive with and rotates in a bearing 64 in the bottom bearing plate 34. The body portion 63 also has a recess 65 for receiving the disk assembly 21.

A body portion and recess in each gear assembly, such as the body portion 63 with its recess 65, represent a motion transfer gear train output. Collectively the gear assemblies, 54, 55 and 56 provide a plurality of spaced parallel motion transfer outputs that rotate about axes parallel to the head axis 15 in FIGS. 1 through 3 in response to rotation of the drive output shaft 43.

Each motion transfer output carries a disk, such as the output represented by the gear assembly 54 and the disk 21, through a universal joint that allows the disk 21 to swivel about its transfer output axis independently of other disks. In one embodiment, this universal joint includes two identical semi-cylindrical bearing blocks 70 and 71 each of which has a partially spherically shaped recess 72 that engages a portion of a spherical head 73 on the disk 21. The disk 21 includes a circular base 74 that connects to the spherical head 73 through a shaft 75.

Figure 7:
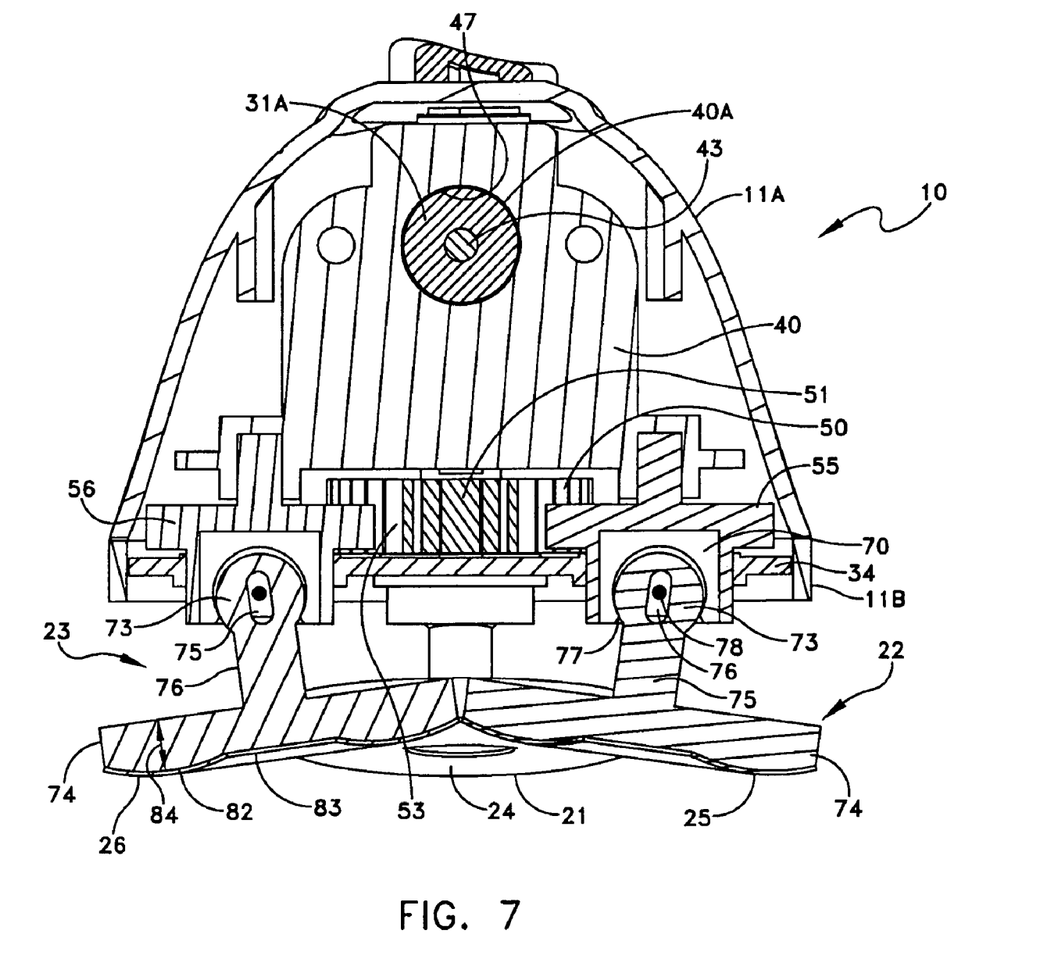
FIG. 7 is a cross-sectional vies taken along lines 7-7 of FIG. 4.

The spherical head 73 includes a vertically elongated slot 76. When assembled, the bearing blocks 70 and 71 surround and loosely capture the spherical head 73 in the recess 72. This loose capture enables the disk 21 to swivel through a solid angle that is limited by interference between the shaft 75 and the bottom edge of the recess. The location of this edge determines the maximum degree of swivel or tilt. In this specific embodiment the bearing blocks 70 and 71 have chamfered bottom edges 77 around the recesses 72 as shown in FIG. 7. Each chamfer 77 is sized to control the maximum degree of swivel or tilt.

When properly positioned in the recess 62, a pin 78 passes through the body portion 63, the blocks 70 and 71 and the slot 76. The pin 78 is affixed to the body portion 63 by press fitting or by other techniques. The slot 76 has a width that is slightly greater than the diameter of the pin 78. Consequently the pin 78 does not interfere with any component of angular motion about the axis of the pin 78. The slot 76 also has a length that assures there is no interference between the spherical head 73 and the pin 78 as to any component of angular motion about an axis normal to the axis of the pin 78. Thus the pin 78 does not limit the maximum degree of swivel. However, as the gear assembly 54 rotates, the pin 78 engages the sides of the slot 76 to rotate the spherical head 73, the attached shaft 75 and the circular base 74 of the disk 21.

Referring again to FIG. 1, it will now be apparent that when an operator energizes the motor 31, each of the disks 21 through 23 rotates generally in the same direction about a transfer output axis that is parallel to the head axis 15 in FIG. 1. Moreover, each of the disks can swivel about its output axis so the individual disks readily adapt to the profile of the skin being processed even without having to manipulate the position of the handle. That is, if an operator does not hold the handle in a specific orientation, adverse effect that would occur without the swivel capability will be negated over a range of misalignment.

Figure 8:
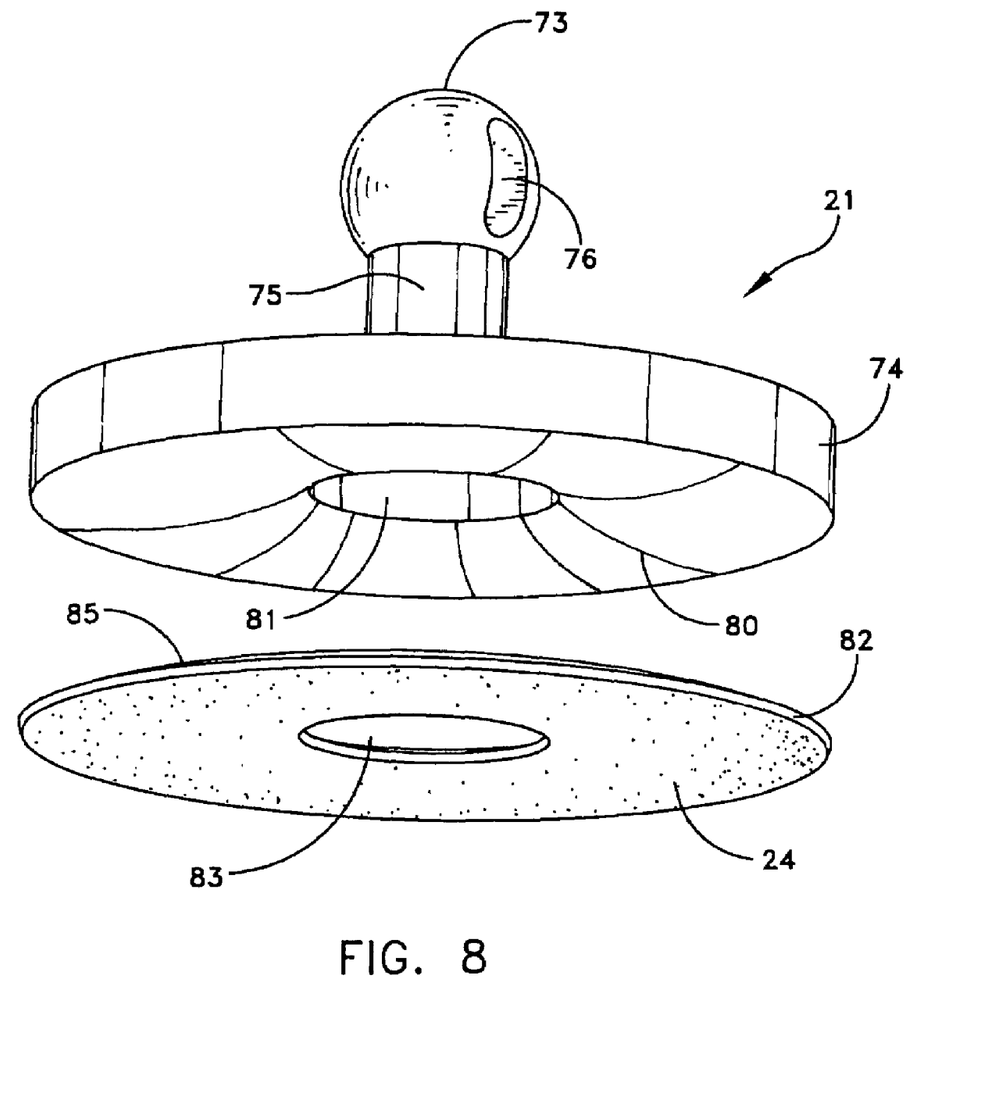
FIG. 8 is a perspective view of a disk and abrasive pad as shown in FIG. 1.

Referring to FIGS. 7 and 8, in one embodiment the disk 21 has an annular support surface 80 with a depressed central region 81. The annular support surface 80 carries the annular pad 24 that has a correspondingly dimensioned annular section 82 and a central opening 83. Thus, when the pad 24 is attached, there is no abrasive material to contact the skin over the central portion of the pad 24.

As a further enhancement, the annular surface 80 is rounded to have a toroidal-like or "doughnut" shape. This is particularly shown in FIGS. 7 and 8 where the annular surface 80 is rounded with a maximum thickness at a radial center 84 of the annular portion of the circular base 74. These rounded, annular surfaces 80 and mounting surfaces 85 of the pads, like the pad 24, are formed with complementary "hook and loop" mating surfaces for quick assembly and disassembly of a pad and disk to facilitate pad replacement. When the surface 85 of a pad 24 attaches to a rounded annular surface 80, the pad conforms to that shape and recesses the edges of the pad 24 from a plane that is tangent to the rounded annular surface 80 at the point 84 of maximum thickness. This rounded shape reduces the chance that the outer periphery of an abrasive pad will dig into the skin to produce irritation.

It will now be seen that this specific embodiment of the invention provides all the advantages and meets all the objectives of this invention. The use of annular abrasive pads that are mounted on rounded annular surfaces and that can swivel greatly facilitates occasional depilation and exfoliation treatments as will occur when a consumer uses the apparatus. The swiveling feature also helps the abrading action because it ensures that the pad is parallel to the skin at the contact area. Annular abrasive pads without any central material minimize the potential for skin irritation caused otherwise by a central portion of a pad drilling into the surface of the skin. Spacing the pads as shown in FIG. 3 minimizes any stress placed on the skin in those closely adjacent portions of the pads that have opposite tangential motion. This apparatus is also readily adapted to low cost manufacture because all the parts, other than the electrical components, are readily molded from various plastics including the gears, shafts and components with bearing surfaces.

It will also be apparent that this embodiment can be varied in a number of different ways and still incorporate this invention. For example, the specific embodiment in FIGS. 1, 2 and 3 discloses a motor shaft axis 13 and a head axis 15 essentially at right angles. Different angles could be substituted and even these two axes could be made coaxial or parallel depending on a particular implementation. The modification of the input gears required for such variations is well known in the art. A specific motion transfer gear train has been disclosed. Other gear and non-gear arrangements could be substituted while still providing the function of converting the motion of a motor output shaft into rotation at three outputs. Further this specific embodiment incorporates three pad positions; other numbers of pad positions could be incorporated. A specific universal joint structure has been disclosed. Other structures could also be substituted. All these variations are well within the capability of a person of ordinary skill in the art once that person has knowledge of this invention. Therefore, it is the intent of the appended claims to cover all such variations and modifications as come within the true spirit and scope of this invention.

What is claimed as new and desired to be secured by Letters Patent of the United States is:

1. Apparatus for abrading hair and exfoliating skin comprising:
   A) housing means for defining the form of said apparatus,
   B) drive means in said housing means for producing rotary motion of a drive means output shaft about a drive axis,
   C) switch means on said housing means for enabling an operator to control the operation of said drive means,
   D) motion transfer means connected to said drive means output shaft for producing rotary motion on each of a plurality of spaced parallel transfer outputs about corresponding output axes,
   E) a disk means for attachment to each parallel transfer output, each disk means having a disk means connection and including a planar disk portion and a shaft terminating in a spherical head,
   F) a universal joint means for coupling rotary motion of each said transfer output to one of said disk means whereby each said disk means can swivel about a corresponding output axis, each spherical head including a slot therethrough and each of said universal joint means including a pin affixed to said transfer means and passing through said slot, and
   G) an abrasive pad attached to each said planar disk portion.

2. Apparatus as recited in claim 1 wherein each of said abrasive pads is annular and each of said disk means includes a raised annular surface for supporting said abrasive pad.

3. Apparatus as recited in claim 2 wherein said raised annular surface is shaped with an edge being recessed from other portions of said abrasive pad.

4. Apparatus as recited in claim 1 wherein each of said disk means has a rounded annular surface for supporting said abrasive pad to present a rounded annular abrasive surface.

5. Apparatus as recited in claim 1 wherein said motion transfer means includes three parallel spaced transfer outputs thereby to provide three spaced disk means.

6. Apparatus as recited in claim 5 wherein said motion transfer means includes an input shaft parallel to said output axes and intersecting said drive axis and interengaging gear means connected to said drive means output shaft and said transfer means input shaft.

7. Apparatus as recited in claim 6 wherein said transfer means includes:
   i. an output gear attached to each of said transfer outputs,
   ii. a drive pinion connected to said input shaft,
   iii. an idler gear for rotating said output gears in response to rotation of said input shaft.

8. Apparatus as recited in claim 6 wherein said transfer means includes:
   i. an output gear attached to each of said transfer outputs,
   ii. a drive pinion connected to said input shaft,
   iii. an idler gear having external teeth for rotating said output gears and internal teeth for engaging said drive pinion, said drive pinion and idler gear having a gear ratio for reducing said transfer output angular velocity over that of said input shaft.

9. Apparatus for abrading hair and exfoliating skin comprising:
   A) a housing for defining the form of said apparatus,
   B) an electric motor in said housing for rotating an electric motor output shaft,
   C) switch means on said housing for enabling an operator to energize said electric motor to operate said apparatus,
   D) three abrasive pad support disks, each having a rounded annular section and having a shaft extending to a slotted spherical head,
   E) a motion transfer gear train including:
      i. an input shaft connected to said electric motor output shaft,
      ii. three spaced driving gears for rotating about three parallel motion transfer gear train output axes,
      iii. an idler gear for rotation about an idler gear axis having a first gear connection to said input shaft and a second gear connection to each of said driving gears whereby energization of said electric motor causes said driving gears to rotate in the same direction and with an angular velocity that is less than the angular velocity of said electric motor output shaft,
      iv. a bearing block on each of said driving gears for capturing said spherical head thereby to maintain a connection between said disk and a corresponding one of said driving gears such that said spherical head retains a freedom to swivel in said block, and
      v. a pin attached to each said driving gear extending through said bearing block and said spherical head thereby to translate rotary motion of said driving gear into rotary motion of said disk, and
   F) an annular abrasive pad affixed to said rounded annular surface section of each of said disks.

* * * * *